(12) United States Patent
Shanmugam et al.

(10) Patent No.: US 11,097,079 B2
(45) Date of Patent: Aug. 24, 2021

(54) COGNITIVELY INDUCING SLEEP CYCLES BY LEVERAGING WEARABLES

(71) Applicant: International Business Machines Corporation, Armonk, NY (US)

(72) Inventors: Dhandapani Shanmugam, Bangalore (IN); Jothi Subramani, Bangalore (IN); Bharath Ganesh, Bangalore (IN); Tuhin Sharma, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 591 days.

(21) Appl. No.: 15/824,514

(22) Filed: Nov. 28, 2017

(65) Prior Publication Data

US 2019/0160251 A1 May 30, 2019

(51) Int. Cl.
*A61M 21/02* (2006.01)
*A61B 5/00* (2006.01)
(Continued)

(52) U.S. Cl.
CPC ........... *A61M 21/02* (2013.01); *A61B 5/4812* (2013.01); *A61B 5/4815* (2013.01);
(Continued)

(58) Field of Classification Search
CPC .......... A61M 21/02; A61M 2021/0072; A61M 2205/3561; A61M 2205/50; A61M 2205/3553; A61M 2205/18; A61M 2230/10; A61M 2021/0044; A61M 2021/0027; A61M 2021/0066; A61M 2021/0022; A61B 5/7275; A61B 5/4836; A61B 5/4812; A61B 5/4815; A61B 5/7267; A61B 5/16; A61B 5/0476; G06F 3/015

See application file for complete search history.

(56) References Cited

U.S. PATENT DOCUMENTS

| 3,576,185 A | 4/1971 | Oskar et al. |
| 3,884,218 A | 5/1975 | Monroe |

(Continued)

OTHER PUBLICATIONS

Gupta et al., "Assisting humans to achieve optimal sleep by changing ambient temperature," arXiv, Dec. 23, 2016, 5 pages, https://arxiv.org/pdf/1612.08645.pdf.
(Continued)

*Primary Examiner* — Kaylee R Wilson
(74) *Attorney, Agent, or Firm* — Peter Edwards

(57) ABSTRACT

A computer-implemented method, system, and computer program product to optimize sleep quality by inducing sleep stages. The method includes: determining a total sleep time; calculating, using the total sleep time, a cycle duration for a sleep cycle, where the sleep cycle includes a first, second, third, fourth, and fifth sleep stage; calculating a first, second, third, fourth, and fifth stage time for the first, second, third, fourth, and fifth sleep stages respectively; generating a first, second, third, fourth, and fifth external parameter for the first, second, third, fourth, and fifth sleep stages respectively, where the external parameters are parameters to facilitate a transition between sleep stages; and executing the first, second, third, fourth, and fifth external parameters upon reaching the calculated stage time for the corresponding sleep stages.

17 Claims, 4 Drawing Sheets

(51) Int. Cl.
  *A61M 21/00*  (2006.01)
  *G06F 3/01*  (2006.01)
  *A61B 5/16*  (2006.01)
  *A61B 5/369*  (2021.01)

(52) U.S. Cl.
  CPC .......... *A61B 5/4836* (2013.01); *A61B 5/7275* (2013.01); *G06F 3/015* (2013.01); *A61B 5/16* (2013.01); *A61B 5/369* (2021.01); *A61B 5/7267* (2013.01); *A61M 2021/0072* (2013.01)

(56) References Cited

U.S. PATENT DOCUMENTS

| | | | |
|---|---|---|---|
| 2007/0287930 A1 | 12/2007 | Sutton | |
| 2013/0234823 A1 | 9/2013 | Kahn et al. | |
| 2015/0306392 A1* | 10/2015 | Sabesan ............... | A61B 5/0205 607/45 |
| 2016/0073951 A1 | 3/2016 | Kahn et al. | |
| 2016/0100696 A1* | 4/2016 | Palashewski ........ | A61B 5/6892 700/90 |
| 2016/0302671 A1* | 10/2016 | Shariff ................... | G16H 50/50 |
| 2017/0368299 A1* | 12/2017 | Kawahara ............. | A61B 5/1114 |

OTHER PUBLICATIONS

Unknown, "Natural Patterns of Sleep," Healthy Sleep, Printed Nov. 17, 2017, 3 pages.

* cited by examiner

COGNITIVELY INDUCING SLEEP CYCLES BY LEVERAGING WEARABLES

BACKGROUND

The present disclosure relates to sleep cycles, and more specifically to optimizing sleep quality by inducing sleep stages.

Sleep cycles consist of two main types of sleep, rapid-eye-movement (REM) sleep and non-rapid-eye-movement (NREM) sleep. NREM sleep is composed of three distinct stages: N1, N2, and N3. The sleep cycle begins with NREM sleep, starting with N1, then transitioning to N2, then to N3, and then to a second N2, then to REM. A complete sleep cycle ends with REM. NREM sleep and REM sleep continue to cycle throughout the course of sleep.

SUMMARY

The present invention provides a computer-implemented method, system, and computer program product to optimize sleep quality by inducing sleep stages. The method may include determining a total sleep time. The method may also include calculating, using the total sleep time, a cycle duration for a sleep cycle, where the sleep cycle includes a first, second, third, fourth, and fifth sleep stage. The method may also include calculating a first, second, third, fourth, and fifth stage time for the first, second, third, fourth, and fifth sleep stages respectively. The method may also include generating a first, second, third, fourth, and fifth external parameter for the first, second, third, fourth, and fifth sleep stages respectively, where the external parameters are parameters to facilitate a transition between sleep stages. The method may also include executing the first, second, third, fourth, and fifth external parameters upon reaching the calculated stage time for the corresponding sleep stages.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
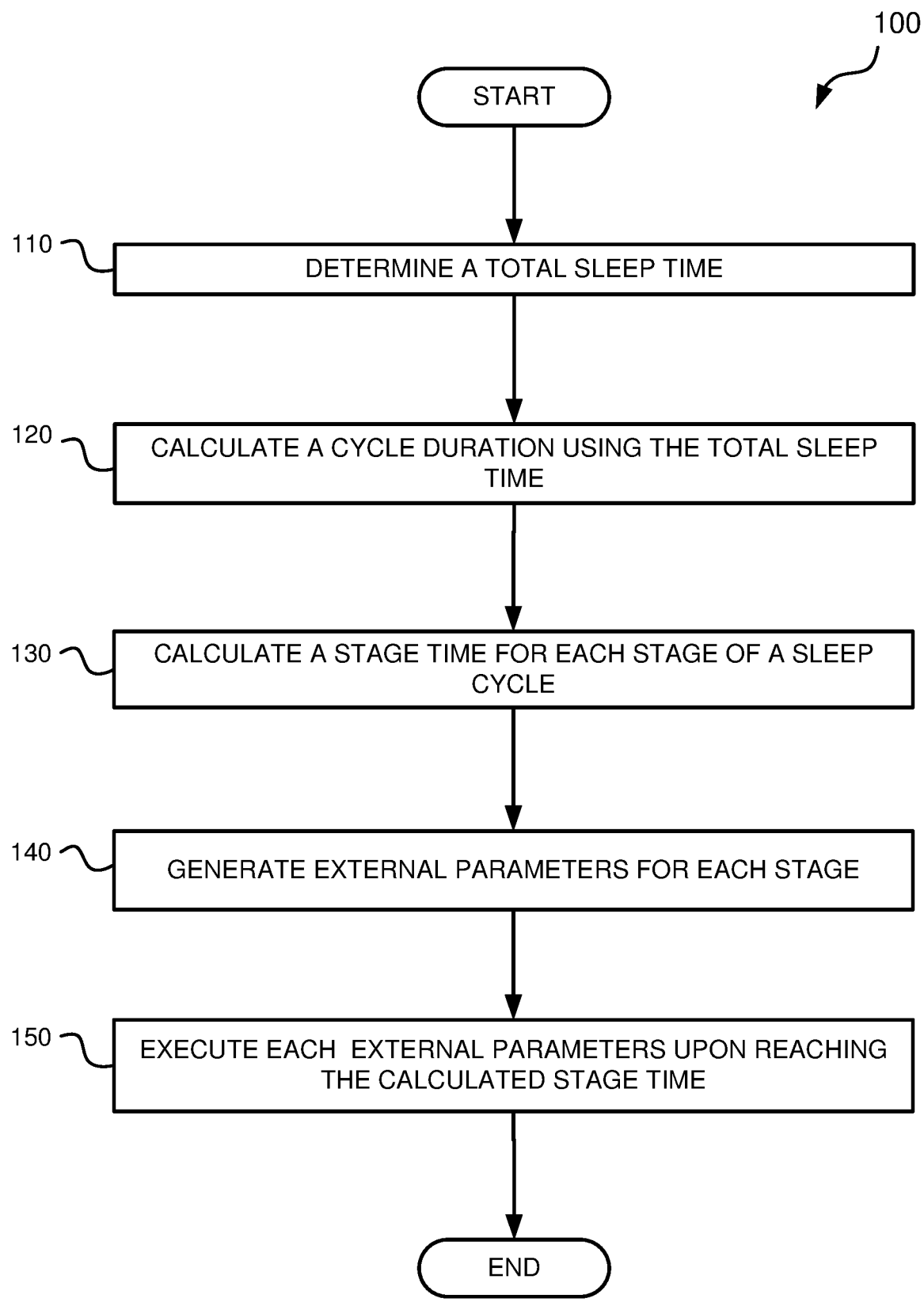
FIG. 1 depicts a flowchart of a set of operations for optimizing sleep quality by inducing sleep stages, according to various embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates to sleep cycles, and more specifically to optimizing sleep quality by inducing sleep stages. While the present disclosure is not necessarily limited to such applications, various aspects of the disclosure may be appreciated through a discussion of various examples using this context.

Sleep deprivation may cause physiological and psychological problems, such as fatigue, sudden weight loss or weight gain, and adverse brain effects. Sleep deprivation and the quality of sleep may have a correlation with a completion of sleep cycles. The benefit of sleep may increase if waking up after a completion of a sleep cycle. Common methods of waking up include using an alarm clock or being woken up by another person. Neither method takes into account when a user gets into sleep or at what point in the sleep cycle a user is in when woken up.

The present disclosure provides a computer-implemented method, system, and computer program product to optimize sleep quality by inducing sleep stages. Sleep stages may be induced using sounds, lights, temperature, and/or vibrations that are modulated by predetermined electroencephalogram (EEG) sleep signals. EEG is a test that measures and records electrical activity of the brain. A length of time for each sleep stage of the sleep cycle may be calculated once a planned length of sleep is known. The sounds, lights, vibrations, temperature etc. are then used to cause a transition, or a change, to the next sleep stage. Existing wearables (e.g., Apple Watch®, Fitbit®, or any other wearable technology) may be used to implement the optimization of sleep quality. Wearable technology includes any smart devices (devices with micro-controllers) that can be worn on the body.

Figure 4:
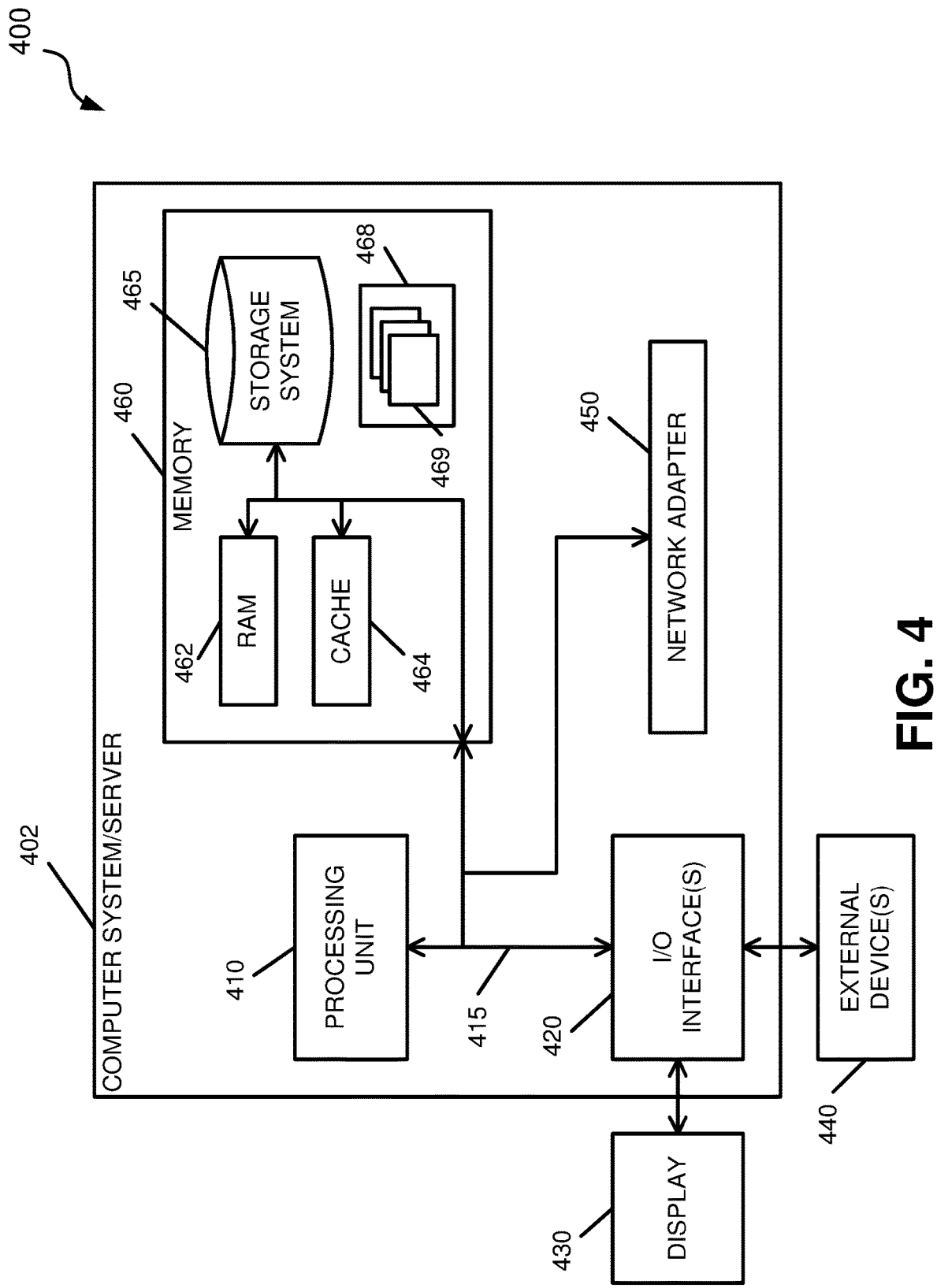
FIG. 4 depicts a block diagram of a sample computer system for implementing operations for determining engagements and patterns of content, according to various embodiments.

Referring now to FIG. 1, a flowchart of a method 100 for optimizing sleep quality by inducing sleep stages is depicted, according to various embodiments. In an embodiment, the method 100 is implemented as a computer script or computer program (e.g., computer executable code) to be executed by a server, on, or connected to, a computer system, such as computer system 400 (FIG. 4). In various embodiments, the server is a connected to a device, such as a wearable device. In some embodiments, the server is a computer program or computer script.

In various embodiments, a server is configured to execute operation 110 to determine a total sleep time. In some embodiments, a user (i.e., a person using the server or device to optimize their sleep) may input their total sleep time. For example, a user may want to sleep for 9 hours, or may have to wake up at 6:00 AM, so the user inputs their desired hours of sleep or desired wake up time. When the user inputs their sleep time, determining the total sleep may include receiving a data packed from an input field of a form on a computing device, the data packet including the total sleep time. The computing device may be a wearable device, or a device used to optimize sleep. In some embodiments, the computing device is a separate device connected to the server. The computing device may communicate with the server via one or more networks (e.g., local area network, wide area network, cloud computing, Internet of Things, etc.).

In some embodiments, the server may communicate (e.g., through the Internet of Things (IoT)) with a user device, to determine a total sleep time. A user device may be a mobile device, an alarm clock, etc. A mobile device may be a portable computing device. Examples of mobile devices may include smartphones, tablets, laptops, wearable devices, personal digital assistants, etc. In various embodiments, the user device must have capabilities to communicate or connect with the server. For example, a user may set an alarm on a mobile device. The server may connect directly with the mobile device to determine a wake up time of the user. The server may then calculate the total sleep time based on the wake up time.

In various embodiments, a server is configured to execute operation 120 to calculate a cycle duration for a sleep cycle using the total sleep time. In some embodiments, the cycle duration is a length of time for a sleep cycle. The cycle duration may be predetermined, or previously known, from past sleep studies. In various embodiments, the sleep cycle includes stages N1, N2, N3, N2, and REM. In some embodiments, N1 may average anywhere between 1-7 minutes, N2 may average between 10-25 minutes, N3 may average between 20-40 minutes, N2 may average between 5-10 minutes, and REM may average between 20-25 minutes, according to previous studies. From this, it may be determined that the average healthy sleep cycle, in this example, runs between 55-108 minutes (i.e., the duration of the sleep cycle is between 55 and 108 minutes).

In various embodiments, the cycle duration is used to calculate the quantity of sleep cycles that occur within the total sleep time. The quantity of sleep cycles may be calculated using the following equation:

$$T = m\left(\frac{a+b+1}{2} + ct\right) \quad (1)$$

, where $\frac{a-b+1}{2} \leq ct \leq \frac{b-a+1}{2}$

In the equation, T is the total sleep time of the user, m is the quantity of sleep cycles, and a and b are a maximum and minimum cycle duration, or length of a sleep cycle. As discussed herein, the average healthy sleep cycle runs between 55-108 minutes (min). Therefore, in some embodiments, a=55 and b=108. When a=55 and b=108, the equation becomes the following:

$$T = m\left(\frac{(55+108+1)}{2} + ct\right) \quad (2)$$

$$T = m(82 + ct) \quad (3)$$

In this equation, ct is a cycle threshold, which may adjust the sleeping cycle duration to avoid non-integer values of m. Adjusting the sleep cycle using the cycle threshold may prevent partial sleep cycles, particularly at the end of the sleep time. As discussed herein, the sleep cycle may range from 55 min-108 min. The equation above includes an average cycle duration of 82 minutes. Depending on the total sleep time of the user, the average cycle duration of 82 minutes may not result in an integer number (i.e., a whole number) of sleep cycles. Any fraction or decimal of a sleep cycle may indicate that a sleep cycle has not been completed, which would result in a non-optimized sleep. To optimize the sleep cycle, the cycle threshold was added to the equation, where the cycle threshold can range between $-27 \leq ct \leq 27$, so that the portion of the equation (82+ct) is the adjusted cycle duration, where the adjusted cycle duration is between 55 min-108 min. In various embodiments, calculating the quantity of sleep cycles includes dividing the total sleep time by the adjusted cycle duration.

For example, a user may have a total sleep time of 420 minutes. In order to have m, the quantity of sleep cycles, be an integer, a cycle threshold value of 2 is added to the equation. In this example, m=420/(82+2), which results in a quantity of cycles of 5, meaning that there are 5 sleep cycles throughout the total sleep time. In another example, the total sleep time is 180 minutes. To result in an integer quantity of sleep cycles, the cycle threshold value may either be 8 or −22. If the threshold value is 8, the quantity of cycles is 2, and if the threshold value is −22, the quantity of cycles is 3.

In some embodiments, when there are multiple options for a threshold value, the threshold value is selected by a user. In other embodiments, the threshold value is determined by the server.

In various embodiments, a server is configured to execute operation 130 to calculate a stage time for each stage of a sleep cycle. The sleep cycle may include a plurality of stages. In various embodiments, the sleep cycle includes stages N1, N2, N3, N2, and REM. In some embodiments, calculating a stage time for each stage of the sleeping cycle includes calculating a stage time for N1, a stage time for N2, a stage time for N3, a stage time for N2, and a stage time for REM.

Calculating a stage time may include determining a particular average stage time of each particular stage of the sleep cycle (e.g., calculating an N1 stage time may include determining an average stage time of all the N1 stages), calculating an average cycle duration using the average stage time of each particular stage (e.g., average N1 stage time, average N2 stage time, average N3 stage time, average N2 stage time, and average REM stage time), calculating a ratio of the average stage time to the average cycle duration, and calculating the stage time for each stage using the cycle duration and the ratio for each particular cycle. The calculated ratios may include a ratio of the N1 average stage time to the average cycle duration, a ratio of the N2 average stage time to the average cycle duration, a ratio of the N3 average stage time to the average cycle duration, a ratio of the N2 average stage time to the average cycle duration, and a ratio of the REM average stage time, each to the average cycle duration. The average cycle duration may be an average duration of a sleep cycle. In some embodiments, the average stage time is determined using the predetermined cycle durations from previous sleep studies. In other embodiments, the average stage time is determined using training data, discussed further herein.

Using the ranges of duration time discussed herein for each sleep stage (N1, N2, N3, N2, REM), the average duration, or average stage time, for each stage may be calculated to be N1=4 min, N2=17.5 min, N3=30 min, N2=7.5 min, and REM=22.5 min.

With the average stage times listed above, the stage time for each stage (e.g., N1 stage time, N2 stage time, N3 stage time, N2 stage time, and REM stage time) may be calculated using the following equations:

$$N1 = \frac{4}{4+17.5+30+7.5+22.5} \times X = \frac{4}{81.5}X \quad (4)$$

$$N2 = \frac{17.5}{4+17.5+30+7.5+22.5} \times X = \frac{17.5}{81.5}X \quad (5)$$

$$N3 = \frac{30}{4+17.5+30+7.5+22.5} \times X = \frac{30}{81.5}X \quad (6)$$

-continued $$N2 = \frac{7.5}{4+17.5+30+7.5+22.5} \times X = \frac{7.5}{81.5}X \quad (7)$$

$$REM = \frac{22.5}{4+17.5+30+7.5+22.5} \times X = \frac{22.5}{81.5}X \quad (8)$$

N1, N2, N3, N2, and REM as depicted in the equations are the stage time for each stage. 81.5 is the average cycle duration using the calculated average stage times of each particular stage. The equations may calculate a ratio of the average stage time to the average cycle duration (e.g., 4/81.5, 17.5/81.5, 30/81.5, 7.5/81.5, and 22.5/81.5) and then multiply the ratio by X, where X is an adjusted cycle duration of a particular sleeping cycle. In some embodiments, X is (82+ct) as discussed herein. When X is (82+ct), the stage time for each stage may be calculated using the following equations:

$$N1 = \frac{4}{81.5}(82+ct) \quad (9)$$

$$N2 = \frac{17.5}{81.5}(82+ct) \quad (10)$$

$$N3 = \frac{30}{81.5}(82+ct) \quad (11)$$

$$N2 = \frac{7.5}{81.5}(82+ct) \quad (12)$$

$$REM = \frac{22.5}{81.5}(82+ct) \quad (13)$$

For example, when a total sleep time is 420 minutes, and the cycle threshold is 2, the duration of each sleep stage, or the stage time of each stage, are calculated to be N1=4.12 min, N2=18.03 min, N3=30.92 min, N2=7.73 min, and REM=23.19 min.

In various embodiments, the average stage time of each stage may be determined using training data. Training data is discussed further herein.

In various embodiments, a server is configured to execute operation 140 to generate a set of external parameters for each stage (e.g., external parameters for N1, external parameters for N2, external parameters for N3, external parameters for N2, and external parameters for REM). The set of external parameters may be parameters to achieve a stage of the sleep cycle. In some embodiments, there are external parameters to transition from N1 to N2, external parameters to transition from N2 to N3, external parameters to transition from N3 to N2, external parameters to transition from N2 to REM, and external parameters to transition from either REM to N1 or REM to consciousness. Examples of external parameters may include sound, light, vibration, and temperature. Generating the set of external parameters is further discussed herein and depicted in FIG. 3.

In various embodiments, a server is configured to execute operation 150 to execute each set of external parameters upon reaching the calculated stage time for the corresponding sleep stage. Executing the set of parameters may include changing a temperature, adjusting or turning on/off lights, adjusting or turning on/off sounds (e.g., music), and/or changing vibrations on a user device or wearable device. In an example, a user is wearing a wearable device on their wrist. When it is time to change stages (based on the calculated stage time), such as from stage N3 to N2, the wearable device may vibrate to pull the user out of the deep sleep. Other example parameters that may pull a user out of a deep sleep may include turning on or increasing harshness of lights, increasing sound, turning on music (e.g., non-soothing music) or other sounds, decreasing the temperature, increasing temperature, etc. In another example, soothing music may play, or lights may be dimmed or turned off, to transition a user into a deeper stage of sleep. These examples are not limiting and are discussed for example purposes only. Any execution of any type of external parameter may be used.

Figure 2:
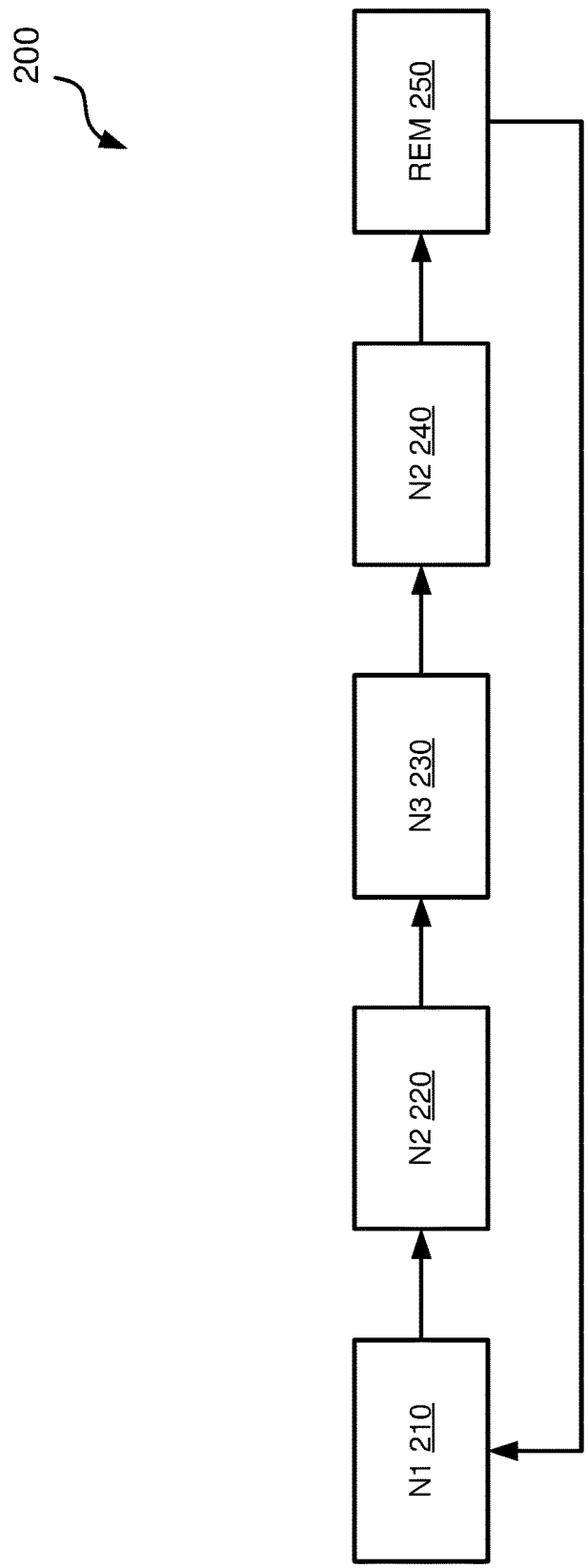
FIG. 2 depicts a block diagram of a sleep cycle, according to various embodiments.

Referring to FIG. 2, a block diagram of a sleep cycle 200 is depicted, according to various embodiments. Sleep cycle 200 may include both REM sleep and NREM sleep. NREM sleep has three stages: N1, N2, and N3. The sleep cycle 200 begins with NREM sleep, starting with N1 210. N1 210 is the lightest stage of NREM sleep, and is a transition stage between consciousness and sleep. The sleep cycle 200 then transitions to N2 220, with N2 220 being a deeper sleep stage than N1 210. The sleep cycle 200 transitions from N2 220 to N3 230, with N3 230 being the deepest sleep stage. N3 230 is a slow wave sleep or a delta-wave sleep. The sleep cycle 200 may then transition to N2 240 sleep, with a user transitioning out of deep sleep. The sleep cycle 200 may end with REM sleep 250. REM sleep 250 is similar to a conscious, or waking, state because of low-voltage brain waves. The sleep cycle 200 is complete after REM 250, but may transition back to sleep stage N1, to start a second sleep cycle and to continue sleeping. The average sleep cycle lasts about 90 minutes; therefore, most people will have multiple sleep cycles throughout their sleeping period.

Figure 3:
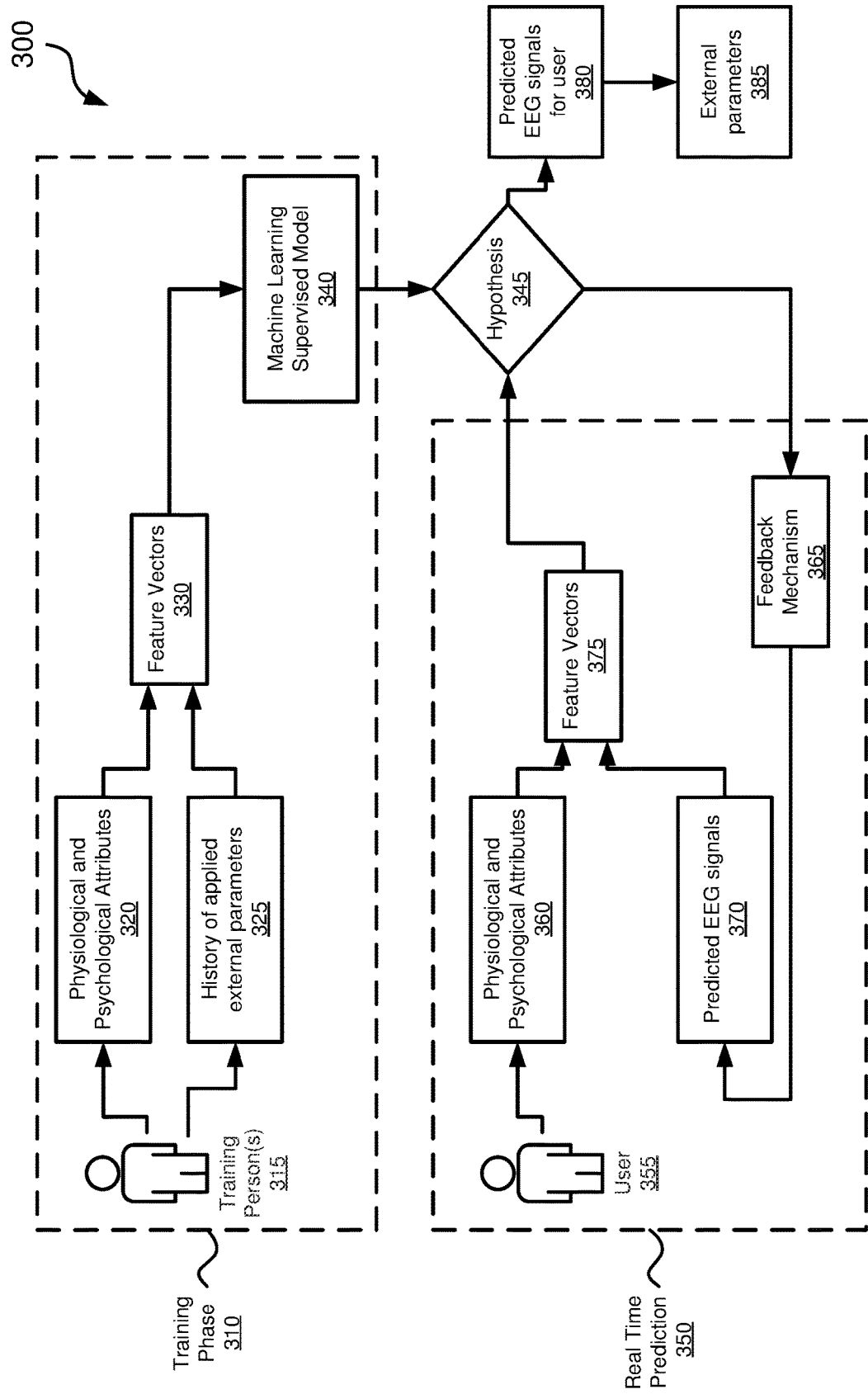
FIG. 3 depicts a flowchart for generating a set of external parameters, according to various embodiments.

Referring to FIG. 3 a flowchart 300 for generating a set of external parameters is depicted, according to various embodiments. In various embodiments, generating a set of external parameters may include a training stage and training data to help form hypotheses or predictions for external parameters.

In various embodiments, generating a set of external parameters includes gathering training data from a training phase 310. In some embodiments, training phase 310 is completed with a variety of training person(s) 315 with various physiological and psychological attributes 320. In other embodiments, training phase 310 is completed with one training person 315, where the training person 315 is the user 355. The training phase 310 may analyze sleeping patterns and gather training data from numerous observations (e.g., more than one thousands) to increase accuracy of the machine learning supervised model 340 and the hypothesis 345. Each observation may span any length of time (e.g., a sleep cycle, a sleep time, a sleep stage, 10 seconds of sleep, 4 hours of sleep, etc.)

In various embodiments, training person(s) 315 are measured for physiological and psychological attributes 320. The physiological attributes (e.g., blood pressure, temperature, heart rate, etc.) may be obtained, or determined, using a kit or a wearable device attached to the training person(s) 315. The psychological attributes (e.g., openness, conscientiousness, extraversion, agreeableness, and neuroticism) may be obtained from a user profile or from certain mental states (e.g., anxiety, depression, etc.) that may be inputted by the user in the user profile. In some embodiments, the user profile may include a set of questions to gauge the psychological attributes of the training person(s) 315.

In various embodiments, training person(s) 315 are measured using an EEG measuring device for EEG signals when various external parameters are applied, or executed, during sleep. The various testing may be documented as a history of applied external parameters 325. In some embodiments, the history of applied external parameters 325 and the training data is categorized based on the corresponding physiological and psychological attributes 320 of the training person(s) 315.

The physiological and psychological attributes 320 and the history of applied external parameters 325 (i.e., training data) may be used to determine feature vectors 330, using known algorithms and/or statistical analysis. Features may be a characteristic of the training data (e.g., physiological and psychological attributes, external parameters, sleep time, sleep cycles, etc.). The features may be converted into a corresponding numerical value (i.e., numerical feature). Feature vectors 330 may be a vector representation of the numerical features. The feature vectors 330 are used with a machine learning supervised model 340 to determine a hypothesis 345. In some embodiments, the machine learning supervised model 340 may use the feature vectors 330 combined with weights to construct a linear predictor function, which is then used to help determine the hypothesis 345. The hypothesis 345 may take the form of a prediction, specifically a prediction of EEG signals of a user. Machine learning supervised model 340 may use the training data and the corresponding feature vectors to improve and increase the accuracy of the linear predictor function. In some embodiments, machine learning supervised model 340 is a neural network that learns, or improves performance, using examples or past data. In various embodiments, machine learning supervised model 340 uses select training data with physiological and psychological attributes 320 corresponding to the physiological and psychological attributes of user 355.

In some embodiments, hypothesis 345 may be determined solely based on the machine learning supervised model 340. The hypothesis 345 may predict EEG signals 380 for the user 355. These predicted EEG signals 380 may then be used to determine external parameters 385.

In other embodiments, a real time prediction phase 350 is occurring real time as a user 355 is using the device to optimize sleep. The real time prediction phase 350 may be subsequent to the training phase 310. The physiological and psychological attributes 360 of the user 355 may be obtained using the methods discussed herein. These physiological and psychological attributes 360 may be used to determine feature vectors 375.

In various embodiments, a feedback mechanism 365 is included in the process, where the feedback mechanism 365 keeps track of already used external parameters so that the user 355 will not become immune to applied external parameters that are based on the predicted EEG signals 370. The predicted EEG signals 370 may be EEG signals that are predicted based on the feedback mechanism 365. In some embodiments, the predicted EEG signals 370 and the physiological and psychological attributes 360 are used to determine feature vectors 375. The feature vectors 375 may be used to update the hypothesis 345, such that the hypothesis 345 may then be used to predict EEG signals 380 and external parameters for the user 355. These predicted EEG signals 380 may then be converted into the external parameters 385.

Referring to FIG. 4, computer system 400 is a computer system/server 402 is shown in the form of a general-purpose computing device, according to various embodiments. The components of computer system/server 402 may include, but are not limited to, one or more processors or processing units 410, a system memory 460, and a bus 415 that couple various system components including system memory 460 to processor 410.

Bus 415 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 402 typically includes a variety of computer system readable media. Such media may be any available media that is accessible by computer system/server 402, and it includes both volatile and non-volatile media, removable and non-removable media.

System memory 460 can include computer system readable media in the form of volatile memory, such as random access memory (RAM) 462 and/or cache memory 464. Computer system/server 402 may further include other removable/non-removable, volatile/non-volatile computer system storage media. By way of example only, storage system 465 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 415 by one or more data media interfaces. As will be further depicted and described below, memory 460 may include at least one program product having a set (e.g., at least one) of program modules that are configured to carry out the functions of embodiments of the invention.

Program/utility 468, having a set (at least one) of program modules 469, may be stored in memory 460 by way of example, and not limitation, as well as an operating system, one or more application programs, other program modules, and program data. Each of the operating system, one or more application programs, other program modules, and program data or some combination thereof, may include an implementation of a networking environment. Program modules 469 generally carry out the functions and/or methodologies of embodiments of the invention as described herein.

Computer system/server 402 may also communicate with one or more external devices 440 such as a keyboard, a pointing device, a display 430, etc.; one or more devices that enable a user to interact with computer system/server 402; and/or any devices (e.g., network card, modem, etc.) that enable computer system/server 402 to communicate with one or more other computing devices. Such communication can occur via Input/Output (I/O) interfaces 420. Still yet, computer system/server 402 can communicate with one or more networks such as a local area network (LAN), a general wide area network (WAN), and/or a public network (e.g., the Internet) via network adapter 450. As depicted, network adapter 450 communicates with the other components of computer system/server 402 via bus 415. It should be understood that although not shown, other hardware and/or software components could be used in conjunction with computer system/server 402. Examples, include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electronic signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object orientated program language such as Smalltalk, C++, or the like, and procedural programming languages, such as the "C" programming language or similar programming languages. The computer readable program instructions may execute entirely one the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   determining a total sleep time desired by a user;
   calculating, using the total sleep time and prior to a start of a sleep cycle, a cycle duration for the sleep cycle, wherein the sleep cycle comprises a first, second, third, fourth, and fifth sleep stage, and wherein the calculating results in an integer number of sleep cycles occurring in the total sleep time desired by the user;
   calculating a first, second, third, fourth, and fifth stage time for the first, second, third, fourth, and fifth sleep stages respectively, resulting in stage times for each sleep stage, wherein calculating the stage times comprises:
      determining an average stage time for each sleep stage respectively, resulting in a first, second, third, fourth, and fifth average stage time;
      calculating an average cycle duration using the first, second, third, fourth, and fifth average stage times;
      calculating a ratio of each average stage time to the average cycle duration, resulting in a first, second, third, fourth, and fifth ratio; and
      calculating the first, second, third, fourth, and fifth stage time by multiplying the cycle duration and the first, second, third, fourth, and fifth ratios respectively;
   generating a first, second, third, fourth, and fifth external parameter for the first, second, third, fourth, and fifth sleep stages respectively, wherein the external parameters are parameters to facilitate a transition between sleep stages, and wherein the generating is based on a training phase that analyzes sleeping patterns and gathers training data from numerous observations for a machine learning model; and
   executing the first, second, third, fourth, and fifth external parameters upon reaching the calculated stage time for the corresponding sleep stages to induce a next sleep stage.

2. The method of claim 1, further comprising:
   calculating a quantity of sleep cycles within the total sleep time using the cycle duration.

3. The method of claim 2, wherein calculating the quantity of sleep cycles comprises:
   determining a cycle threshold, wherein the cycle threshold adjusts the cycle duration, resulting in an adjusted cycle duration; and
   calculating the quantity of sleep cycles by dividing the total sleep time by the adjusted cycle duration.

4. The method of claim 1, wherein the first, second, third, fourth, and fifth average stage times are determined based on predetermined cycle durations.

5. The method of claim 1, wherein the first, second, third, fourth, and fifth average stage times are determined based on the training data.

6. The method of claim 1, wherein generating the first, second, third, fourth, and fifth external parameters comprises:
   gathering the training data;
   determining physiological and psychological attributes of the user;
   selecting training data with physiological and psychological attributes corresponding to the physiological and psychological attributes of the user; and
   predicting the external parameters based on the selected training data.

7. The method of claim 6, wherein the machine learning model is a supervised machine learning model.

8. The method of claim 6, wherein the training data is data gathered from analyzing sleeping patterns of a plurality of users.

9. The method of claim 1, wherein the set external parameters include at least one of sound, light, vibration, and temperature.

10. The method of claim 1, wherein calculating the first, second, third, fourth, and fifth stage time comprises:
    calculating a specific duration of time for each of the first, second, third, fourth, and fifth stage times of the cycle duration for the user, wherein the calculating results in the integer number of sleep cycles occurring in the total sleep time desired by the user.

11. A system having one or more computer processors, the system configured to:
    determine a total sleep time desired by a user;
    calculate, using the total sleep time and prior to a start of a sleep cycle, a cycle duration for the sleep cycle, wherein the sleep cycle comprises a set of sleep stages, and wherein the calculating results in an integer number of sleep cycles occurring in the total sleep time desired by the user;
    calculate a particular stage time for each particular stage of the set of sleep stages, wherein calculating the particular stage time for each particular stage of the set of sleep stages comprises:
       determining a particular average stage time of each particular stage;
       calculating an average cycle duration using the particular average stage times;
       calculating a particular ratio for each particular average stage time to the average cycle duration; and
       calculating the particular stage time for each particular stage by multiplying the cycle duration and each particular ratio respectively;
    generate a particular external parameter for each particular stage, wherein the external parameters are parameters to facilitate a transition between sleep stages, and wherein the generating is based on a training phase that analyzes sleeping patterns and gathers training data from numerous observations for a machine learning model; and
    execute each particular external parameter upon reaching the particular stage time for the corresponding sleep stages to induce a next sleep stage.

12. The system of claim 11, further configured to:
    calculate a quantity of sleep cycles within the total sleep time using the cycle duration.

13. The system of claim 12, wherein calculating the quantity of sleep cycles comprises:
    determining a cycle threshold, wherein the cycle threshold adjusts the cycle duration, resulting in an adjusted cycle duration; and
    calculating the quantity of sleep cycles by dividing the total sleep time by the adjusted cycle duration.

14. The system of claim 11, wherein generating the particular external parameters for each stage comprises:
    gathering the training data;
    determining physiological and psychological attributes of the user;
    selecting training data with physiological and psychological attributes corresponding to the physiological and psychological attributes of the user; and predicting the external parameters based on the selected training data.

15. A computer program product comprising a non-transitory computer readable storage medium having program instructions embodied therewith, the program instructions executable by a processor to cause the processor to perform a method, the method comprising:

determining a total sleep time desired by a user;

calculating, using the total sleep time and prior to a start of a sleep cycle, a cycle duration for the sleep cycle, wherein the sleep cycle comprises a first, second, third, fourth, and fifth sleep stage, and wherein the calculating results in an integer number of sleep cycles occurring in the total sleep time desired by the user;

calculating a first, second, third, fourth, and fifth stage time for the first, second, third, fourth, and fifth sleep stages respectively, resulting in stage times for each sleep stage, wherein calculating the stage times comprises:

determining an average stage time for each sleep stage respectively, resulting in a first, second, third, fourth, and fifth average stage time;

calculating an average cycle duration using the first, second, third, fourth, and fifth average stage times;

calculating a ratio of each average stage time to the average cycle duration, resulting in a first, second, third, fourth, and fifth ratio; and calculating the first, second, third, fourth, and fifth stage time by multiplying the cycle duration and the first, second, third, fourth, and fifth ratios respectively;

generating a first, second, third, fourth, and fifth external parameter for the first, second, third, fourth, and fifth sleep stages respectively, wherein the external parameters are parameters to facilitate a transition between sleep stages, and wherein the generating is based on a training phase that analyzes sleeping patterns and gathers training data from numerous observations for a machine learning model; and executing the first, second, third, fourth, and fifth external parameters upon reaching the calculated stage time for the corresponding sleep stages to induce a next sleep stage.

16. The computer program product of claim 15, further comprising:

calculating a quantity of sleep cycles within the total sleep time using the cycle duration.

17. The computer program product of claim 16, wherein calculating the quantity of sleep cycles comprises:

determining a cycle threshold, wherein the cycle threshold adjusts the cycle duration, resulting in an adjusted cycle duration; and calculating the quantity of sleep cycles by dividing the total sleep time by the adjusted cycle duration.

* * * * *